United States Patent [19]

Relyea et al.

[11] 4,335,142
[45] Jun. 15, 1982

[54] ARYL (1-ARYLSULFONYL) VINYL SULFONES

[75] Inventors: Douglas I. Relyea; Robert A. Davis, both of New Haven, Conn.

[73] Assignee: Uniroyal, Inc., New York, N.Y.

[21] Appl. No.: 74,271

[22] Filed: Sep. 11, 1979

[51] Int. Cl.³ .................... C07C 147/06; A01N 31/08
[52] U.S. Cl. ........................................ 424/337; 568/29
[58] Field of Search .................... 260/609 E, 607 AR; 424/337; 568/29

[56] References Cited

U.S. PATENT DOCUMENTS

| | | | |
|---|---|---|---|
| 3,242,041 | 3/1966 | Aichenegg et al. | 424/337 |
| 3,629,438 | 12/1971 | von Schmeling et al. | 424/275 |
| 3,682,212 | 8/1972 | Relyea | 260/330.5 |

FOREIGN PATENT DOCUMENTS 2005256  8/1970  Fed. Rep. of Germany ... 260/609 E

OTHER PUBLICATIONS

F. Montanaii et al., Chem. Abstracts 52:9987, (1958).
F. Tantasheva et al. Zh. Org. Khim., Mar. 1978, 14(3), 478–484, Addition of Sulfene Chlorides to Vinyl Sulfones.
Hackh's Chem. Dictionary, p. 427, Fourth Edition, (1972).

*Primary Examiner*—Mary C. Lee
*Attorney, Agent, or Firm*—Anthony Lagani, Jr.

[57] ABSTRACT

A microbicide having the general formula

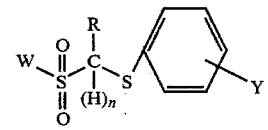

wherein R is a halomethyl radical, or a methylene radical; W is cyclohexyl, phenyl or meta or para substituted phenyl wherein the substituents are $C_1$–$C_4$ alkyl, halogen or nitro; X and Y is hydrogen, $C_1$–$C_4$ alkyl, halogen or nitro; provided that when R is halomethyl n is 1 and when R is methylene n is 0.

21 Claims, No Drawings

ARYL (1-ARYLSULFONYL) VINYL SULFONES

BACKGROUND OF THE INVENTION

It is well known that certain sulfones are useful as microbicides. For example compounds of the general formula

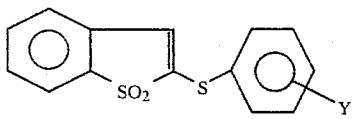

wherein Y is hydrogen, or a substituent in the meta or para position selected from the group consisting of $C_1$–$C_4$ alkyl, halogen and nitro. These compounds, however, have limited effectiveness. Additionally, they are susceptible to photodegradation. Hence, their useful life under outdoor use conditions is limited; see for example U.S. Pat. No. 3,629,438 and 3,686,216.

Other sulfones are taught in U.S. Pat. No. 3,242,041 of the general formula

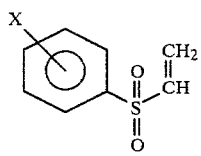

wherein X is defined as being the same as Y above. Again these compounds have limited effectiveness as microbicides.

SUMMARY OF THE INVENTION

It has surprisingly been found that novel sulfones of the general formula

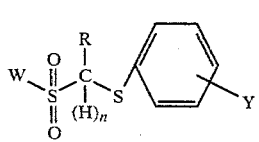

wherein R is a halomethyl radical and n is 1, or a methylene radical and n is 0 W is cyclohexyl, phenyl or meta or para substituted phenyl wherein the substituents are $C_1$–$C_4$ alkyl, halogen or nitro, Y is hydrogen or $C_1$–$C_4$ alkyl, halogen or nitro are effective microbicides.

The microbicides of this invention may be used in a solvent vehicle or may be applied to plants as an emulsion.

DETAILED DESCRIPTION OF THE INVENTION

This invention relates to sulfones which are useful as microbicides. More particularly it relates to sulfones of the general formula

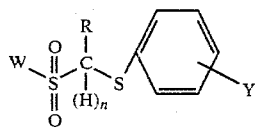

wherein R is a halomethyl radical and n is 1, or a methylene radical and n is 0 W is cyclohexyl, phenyl or meta or para substituted phenyl wherein the substituents are $C_1$–$C_4$ alkyl, halogen or nitro, Y is hydrogen or $C_1$–$C_4$ alkyl, halogen or nitro.

The preferred halogens are chlorine or bromine. The novel sulfones of this invention are prepared by reacting a phenyl vinyl sulfone of the general formula

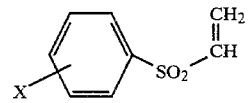

wherein X is as previously defined, with a phenyl sulfenyl halide of the general formula

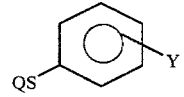

wherein Y is as previously defined and Q is halogen. The reaction product is an adduct of the general formula

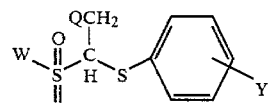

wherein Y, Q and W are as previously defined.

The adduct may be dehydrohalogenated by any suitable means to form the vinyl analog of the general formula

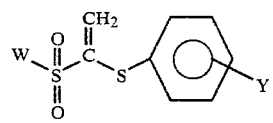

wherein W and Y are as previously defined. Preferably, dehydrohalogenation is carried out in tetrahydrofuran solution using methylamine as the acid acceptor. The reaction proceeds at ambient temperatures. This vinyl compound exhibits microbicidal effectiveness superior to that of related prior art compounds. As used in the specification and claims the term "Olefin Sulfide" means the foregoing vinyl compound of this invention.

The microbicides of this invention may be applied to the locus under attack by microbes either from solution or water emulsion. Illustrative, non-limiting examples of suitable solvents which may be used in the application of the microbicides of this invention are acetone, methanol, ethanol, isopropyl alcohol, t-butyl alcohol, cyclohexanol, cyclohexanone, n-butyl alcohol, toluene, xylene, dioxane, dimethyl formamide, dimethylsulfoxide, ethylene chloride, diacetone alcohol and n-methylpyrrolidone. Water emulsions prepared from these solutions may also be applied to a locus under attack by microbes.

The microbicides of this invention are generally applied at a rate of about 0.1 to about 20 pounds per acre; more preferably about 0.3 to about 2 pounds per acre.

Where solutions or emulsions are prepared the concentration of microbicide in solution is about 0.002 weight percent to about 2 weight percent; more preferably 0.02 to about 0.2 weight percent.

The method of preparation and structure of preferred compounds of this invention may be more readily appreciated by reference to the following examples.

EXAMPLE 1

PREPARATION OF 2-CHLORO-1-(PHENYLSULFONYL)ETHYL PHENYL SULFIDE

To a solution of 9.0 g (53.5 millimoles) of phenyl vinyl sulfone in 50 ml of glacial acetic acid at 25° C. was added 7.8 g (54 millimoles) of benzenesulfenyl chloride. The clear orange solution was allowed to stand 16 hours at 23°–25° C. in a 250 ml flask protected from atmospheric moisture by a drying tube. During that time the color of the reaction mixture changed to a pale yellow. The solution was poured into 500 ml of distilled water. The mixture was extracted with four 50 ml portions of distilled water and dried over 7 g of anhydrous magnesium sulfate. Removal of the chloroform solvent by evaporation at reduced pressure gave 16.6 g of heavy, pale yellow oil.

Amal. Calcd. for $C_{14}H_{13}ClO_2S_2$: C,53.75; H,4.19; Cl,11.33; S,20.50. Found: C,53.85; H,4.36; Cl,11.19; S,20.56.

EXAMPLE 2

PREPARATION OF PHENYL 1-(PHENYLSULFONYL)VINYL SULFIDE

A solution of 31.2 g (0.100 mole) of 2-chloro-1-(phenylsulfonyl)ethyl sulfide in 100 ml of anhydrous ether at 25° C. was treated with 8 g (0.1 mole) of reagent pyridine. There was a 4° C. exotherm and a crystalline precipitate began to separate from the solution. The reaction mixture was allowed to stand 16 hours. The colorless crystals were separated by filtration, washed with ether and dried to give 11.2 g (98%) of pyridine hydrochloride. The ether solution was washed twice with 100 ml of water, once with 100 ml of 5% hydrochloric acid, twice more with 100 ml portions of water, and then dried over anhydrous magnesium sulfate. Removal of the ether by evaporation under vacuum, first at 30° (15 mm) and then at 76° (0.01 mm) gave 24.6 g (89%) of pale tan oil.

Anal. Cald'd. for $C_{14}H_{12}O_2S_2$: C,60.84; H,4.38; S,23.20. Found: C,60.48; H,4.74; S,23.17.

EXAMPLE 3

PREPARATION OF 2-CHLORO-1-(p-TOLYLSULFONYL)ETHYL PHENYL SULFIDE

A solution of 36.4 g (0.200 mole) of p-tolyl vinyl sulfone in 200 ml of glacial acetic acid was treated with 29.5 g (0.204 mole) of benzenesulfenyl chloride. The initial temperature of the clear red solution was 21° C. An exotherm occurred producing a maximum temperature of 28.5° at 50 minutes after mixing the reactants. The reaction mixture was allowed to stand for 64 hours. Removal of the acetic acid by evaporation at reduced pressure gave a residue of 60 g, m.p. 68°–80° C. Recrystallization from 50 ml of dioxane and 25 ml of pentane gave a first crop of 24 g (37%), m.p. 85.0°–86.5° C. and a second crop of 9.3 g (14%), m.p. 84°–86° C.

Anal. Calc'd. for $C_{15}H_{15}ClO_2S_2$: C,55.12; H,4.63; Cl,10.85; S,19.62. Found: C,55.29; H,4.86; Cl,10.92; S,18.66.

EXAMPLE 4

PREPARATION OF PHENYL 1-(p-TOLYLSULFONYL)VINYL SULFIDE

Fifty millimoles (16.3 g) of 2-chloro-1-(p-tolylsulfonyl) ethyl phenyl sulfide was dissolved in 30 ml of dioxane. The solution was diluted with 100 ml of ether and treated with 5.0 ml (62 millimoles) of reagent pyridine. The solution became cloudy in two minutes and crystalline solid began to separate in five minutes. Filtration at the end of five hours separated 4.99 g (86%) of pyridine hydrochloride. The filtrate was washed with 25 ml portions of the following: water, water, 10% hydrochloric acid, and water. Evaporation of the solvent under reduced pressure gave 14.5 g (100%) of light tan oil, $n^{20}$ 1.6044, $d_{25}^{25}$ 1.241.

Anal. Calc'd. for $C_{15}H_{14}O_2S_2$: C,62.05; H,4.86; S,22.07. M.R., 81.88. Found: C,60.21; H,4.78; S,20.39. M.R., 80.53.

The proton magentic resonance spectrum measured in carbon tetrochloride at 25° supports the assigned structure. Peaks were observed for methyl ($\delta=2.93$ 3 protons), ethylidene ($\delta=5.63$ and 6.57, 2 protons), phenyl ($\delta=7.16$, 5 protons) and phenylene ($\delta=7.26$, 2 protons), ortho to methyl ($\delta=7.67$, 7.75, 2 protons, ortho to methyl).

EXAMPLE 5

PREPARATION OF 2-CHLORO-1-(PHENYLSULFONYL)ETHYL m-TOLYL SULFIDE

A solution of 33.6 g (0.200 mole) of phenyl vinyl sulfone in 100 ml of glacial acetic acid at 23° was treated with 34.3 g (0.216 mole) of m-toluenesulfenyl chloride. There was an exotherm to 40° in five minutes. The reaction mixture was allowed to stand for sixteen hours. The solvent was evaporated at reduced pressure and the residue recrystallized from 100 ml of ethyl acetate-petroleum ether (1:1) to give 28 g (43%) of a first crop, m.p. 77°–78°.

Anal. Calc'd. for $C_{15}H_{15}ClO_2S_2$: C,55.12; H,4.62; S,19.62. Found: C,55.21; H,4.65; S,18.91

EXAMPLE 6

PREPARATION OF 2-CHLORO-1-(p-CHLOROPHENYLSULFONYL)-ETHYL PHENYL SULFIDE

A solution of 29.4 g (0.145 mole) of p-chlorophenyl vinyl sulfone in 50 ml of carbon tetrachloride at 22° was treated with 21.0 g (0.145 mole) of benzenesulfenyl chloride. There was an exotherm to 32°. The solution was removed at reduced pressure and the residue recrystallized from benzene to give product of m.p. 108.5°–109.5° C.

Anal. Calc'd. for $C_{14}H_{12}Cl_2O_2S_2$: C,48,42; H,3.48; Cl,20.42; S,18.47. Found: C,47.78; H,3.46; Cl,20.43; S,18.26.

EXAMPLE 7

PREPARATION OF 2-CHLORO-1-(m-NITROPHENYLSULFONYL)-ETHYL PHENYL SULFIDE

In a mixture of 50 ml of glacial acetic acid and 100 ml of carbon tetrachloride at 56° was dissolved 30.9 g (0.145 mole) of m-nitrophenyl vinyl sulfone. Addition of 21.0 g (0.145 mole) of benzenesulfenyl chloride produced an exotherm to 58°. The clear solution was allowed to stand for seventy hours. Removal of the solvent by evaporation at reduced pressure and recrystallization of the residue from toluene gave yellow needles, m.p. 125.5°–126.5°.

Anal. Calc'd. for $C_{14}H_{12}ClNO_4S_2$: C,46.99; H,3.38; Cl,9.91; N,3.91; S,17.92. Found: C,46.95; H,3.49; Cl,9.87; N,3.93; S,18.09.

EXAMPLE 8

PREPARATION OF 2-CHLORO-1-(p-TOLYLSULFONYL)ETHYL p-BROMOPHENYL SULFIDE

A solution of 26.8 g (0.147 mole) of p-tolyl vinyl sulfone in 50 ml of carbon tetrachloride was treated with 32.8 g (0.146 mole) of p-bromobenzenesulfenyl chloride. There was an exotherm from 25° to 29° in one hour. The mixture was allowed to stand 72 hours. The solvent was removed at reduced pressure and the residue recrystallized from ethyl acetate-petroleum ether (1:1) to give colorless needles, m.p. 82.5°–84.0°.

Anal. Calc'd. for $C_{15}H_{14}BrClO_2S_2$: C,44.40; H,3.47. Found: C,44.46; H,3.47.

EXAMPLE 9

PREPARATION OF 2-CHLORO-1-(PHENYLSULFONYL)ETHYL p-BROMOPHENYL SULFIDE

A solution of 24.8 g (0.147 mole) of phenyl vinyl sulfone in 50 ml of carbon tetrachloride and 25 ml of glacial acetic acid at 28° was treated with 32.8 g (0.146 mole) of p-bromobenzenesulfenyl chloride. A 4° exotherm occurred. The reaction mixture was allowed to stand for 72 hours. The solvent was removed by evaporation at reduced pressure. The residue was recrystallized from 50 ml of benzene to give colorless needles, m.p. 97.5°–98.5°.

Anal. Calc'd. for $C_{14}H_{12}BrClO_2S_2$: C,42.92; H,3.09; Br+Cl,29.44; S,16.37. Found: C,42.67; H,3.06; Br+Cl,29.01; S,16.75.

EXAMPLE 10

PREPARATION OF 2-CHLORO-1-(p-TOLYLSULFONYL)ETHYL m-NITROPHENYL SULFIDE

A solution of 0.642 mole of m-nitrobenzenesulfenyl chloride in enough carbon tetrachloride to make 1060 ml was prepared by passing chlorine for 6.5 hours into a solution of 99 g (0.321 mole) of bis(m-nitrophenyl)disulfide in 1 liter of carbon tetrachloride at 45° C. One-quarter of this solution (265 ml, equivalent to 0.161 mole of the sulfenyl chloride) was treated with 29.2 g (0.160 mole) of p-tolyl vinyl sulfone. Upon standing for several weeks crystals separated. Filtration gave 18 g (30%) of crude product m.p. 92°–101°. Recrystallization from 30 ml of ethyl acetate gave pure material m.p. 103.5°–104.5°.

Anal. Calc'd. for $C_{15}H_{14}ClNO_4S_2$: C,48.45; H,3.79; Cl,9.53; N,3.77; S,17.24. Found: C,48.48; H,3.85; Cl,9.50; N,3.72; S,17.10.

EXAMPLE 11

PREPARATION OF 2-CHLORO-1-(p-CHLOROPHENYLSULFONYL)-ETHYL p-BROMOPHENYL SULFIDE

To a solution of 29.8 g (0.146 mole) of p-chlorophenyl vinyl sulfone in 50 ml of carbon tetrachloride at 25° C. was added 32.8 g (0.146 mole) of p-bromobenzenesulfenyl chloride. There was an exotherm of 4° within 52 minutes. The reaction mixture was allowed to stand for three days. Solvent was removed by evaporation at reduced pressure. The residue was recrystallized from 60 ml of ethyl acetate-petroleum ether (1:1) to give colorless needles, m.p. 76°–78°.

Anal. Calc'd. for $C_{14}H_{11}BrCl_2O_2S_2$: C,39.45; H,2.60; Br+Cl,35.39. Found: C,39.04; H,2.62; BrCl,35.09.

EXAMPLE 12

PREPARATION OF 2-CHLORO-1-(m-NITROPHENYLSULFONYL)p-BROMOPHENYL SULFIDE

A solution of 31.3 g (0.147 mole) of m-nitrophenyl vinyl sulfone in 50 ml of carbon tetrachloride and 75 ml of acetic acid at 44° C. was treated with 32.8 g (0.146 mole) of p-bromobenzenesulfenyl chloride. After three days the solvent was removed by reduced pressure evaporation and the residue was recrystallized from 70 ml of toluene to give light yellow needles, m.p. 137°–138°.

Anal. Calc'd. for $C_{14}H_{11}BrClNO_4S_2$: C,38.50; H,2.54; N,3.21; Br+Cl,26.42. Found: C,38.68; H,2.53; N,3.30; Br+Cl,26.42.

EXAMPLE 13

PREPARATION OF 2-CHLORO-1-(PHENYLSULFONYL)ETHYL p-t-BUTYLPHENYL SULFIDE

A solution of 25.2 g (0.150 mole) of phenyl vinyl sulfone in 100 ml of carbon tetrachloride and 30 ml of glacial acetic acid was treated with 30.1 g (0.150 mole) of p-t-butylbenzenesulfenyl chloride. There was an exotherm of 2° within 10 minutes. The red color of the sulfenyl chloride disappeared within 24 hours. Evaporation of the solvent left 54 g (98%) of crude product m.p. 58°–69°. Recrystallization from 100 ml of ethyl acetate-petroleum ether (1:1) gave 29 g (52%) of colorless crystals, m.p. 67°–69°.

Anal. Cald'd. for $C_{18}H_{21}ClO_2S_2$: C,58.60; H,5.74; Cl,9.61; S,17.38. Found: C,58.62; H,5.73; Cl,9.64; S,17.19.

EXAMPLE 14

PREPARATION OF 2-CHLORO-1-(p-CHLOROPHENYLSULFONYLETHYL m-NITROPHENYL SULFIDE

A solution of 0.161 mole of m-nitrobenzenesulfenyl chloride in enough carbon tetrachloride to make 265 ml was treated with 32.4 g of p-chlorophenyl vinyl sulfone. The reaction mixture was allowed to stand several weeks at room temperature in a closed flask. Off-white granules crystallized out. Filtration, washing with ethyl acetate-petroleum ether, and drying gave a pure product, m.p. 114.5°–115.5°.

Anal. Calc'd. for $C_{14}H_{11}Cl_2NO_4S_2$: C,42.87; H,2.83; N,3.57; Cl,18.08. Found: C,42.87; H,2.58; N,3.62; Cl,18.21.

EXAMPLE 15

PREPARATION OF 2-CHLORO-1-(m-NITROPHENYLSULFONYL)-ETHYL m-NITROPHENYL SULFIDE

To a solution of 0.161 mole of m-nitrobenzenesulfenyl chloride in enough carbon tetrachloride to make 265 ml was added 34.1 g (0.160 mole) of m-nitrophenyl vinyl sulfone. The reaction mixture was allowed to stand at room temperature in a closed flask for several weeks. Evaporation of the solvent under reduced pressure gave 44 g (68%) of crude product m.p. 98°–110°. Recrystallization from 120 ml of toluene gave 23 g (36%) of pure product, m.p. 105.0°–106.5°.

Anal. Calc'd. for $C_{14}H_{11}ClN_2O_6S_2$: C,41.74; H,2.75; Cl,8.80; N,6.95; S,15.92. Found: C,42.10; H,2.94; Cl,8.56; N,6.85; S,15.63.

EXAMPLE 16

PREPARATION OF 2-CHLORO-1-(p-TOLYLSULFONYL)ETHYL m-TOLYL SULFIDE p-Tolyl vinyl sulfone (27.3 g, 0.150 mole) was dissolved in 100 ml of reagent carbon tetrachloride to give a clear solution at 32° C. Addition of 27.3 g (0.172 mole) of m-toluenesulfenyl chloride gave a bright red solution. The exothermic reaction raised the temperature to 44° C. in ten minutes. The color faded to bright orange in 16 hours. Several weeks' standing at room temperature in a closed flask produced crystals. Filtration gave 19.5 g of crude product m.p. 80°–97°. Recrystallization from 50 ml of ethyl acetate-pentane (7:3) gave 13.8 g (27%) of pure product, m.p. 99.5°–100.5°.

Anal. Calc'd for $C_{16}H_{17}ClO_2S_2$: C,56.37; H,5.02; Cl,10.40; S,18.81. Found: C,56.43; H,5.17; Cl,10.39; S,18.79.

EXAMPLE 17

2-CHLORO-1-(CYCLOHEXYLSULFONYL)ETHYL PHENYL SULFIDE

To a solution of 174.3 g (1.00 mole) of cyclohexyl vinyl sulfone in 1000 ml of glacial acetic acid was added, all in one portion, 116 ml (144.6 g, 1.00 mole) of benzenesulfenyl chloride. The exotherm raised the temperature of the reaction mixture from 25° to 41° C. The solution was allowed to stand for 16 hours. Most of the acetic acid was removed by evaporation at reduced pressure. The remaining acetic acid was removed by coevaporation with two 50 ml portions of toluene. The residue was finally dried at 25° (0.01 mm) to give a pale yellow oil, $n^{20}$ 1.5760.

Anal. Calc'd. for $C_{14}H_{19}ClO_2S_2$: C,52.73; H,6.01; S,20.11. Found: C,53.03; H,5.98; S,19.45.

EXAMPLE 18

PREPARATION OF 2-CHLORO-1-(p-CHLOROPHENYLSULFONYL)-ETHYL p-t-BUTYLPHENYL SULFIDE

To a solution of 26.1 g (0.129 mole) of p-chlorophenyl vinyl sulfone in 100 ml of carbon tetrachloride at 25° C. was added 25.9 (0.129 mole) of p-t-butylbenzenesulfenyl chloride. The reaction mixture was allowed to stand for six days in a closed flask. Removal of the solvent by evaporation gave 55 g (106%) of crude product, m.p. 52°–68°. Recrystallization from 300 ml ethylacetatepentane (1:5) gave 31.5 g (61%) of pure product, m.p. 65°–67°.

Anal. Calc'd. for $C_{18}H_{20}Cl_2O_2S_2$: C,53.60; H,5.00; Cl,17.58; S,15.90. Found: C,54.01; H,5.06; Cl,17.17; S,15.59.

EXAMPLE 19

PREPARATION OF 2-CHLORO-1-(p-t-BUTYLPHENYLSULFONYL)-ETHYL PHENYL SULFIDE

To a solution of 21.0 g (93.7 moles) of p-t-butylphenyl vinyl sulfone in 100 ml of methylene chloride at 20° C. was added 14.0 ml (17,5 g, 121 mmoles) of benzenesulfenyl chloride. After 75 minutes the initial red color of the solution had changed to orange. In the same time the temperature of the solution rose to 26° C. After three days at 23° C. the solvent was removed by evaporation. The semicrystalline residue was recrystallized from ethyl acetate-pentane (1:2) to give a first crop of 18.3 g (53%), m.p. 104.0°–105.5° C. and subsequent crops of 8.3 and 3.0 g, for a total yield of 86%.

Anal. Calc'd. for $C_{18}H_{21}ClO_2S_2$: C,58.60; H,5.74; Cl,9.61; S,17.38. Found: C,57.00; H,5.55; Cl,9.66; S,17.63.

EXAMPLE 20

PREPARATION OF 2-CHLORO-1-(PHENYLSULFONYL)ETHYL p-CHLOROPHENYL SULFIDE

A solution of 42 g (0.286 mole) of phenyl vinyl sulfone in 200 ml of carbon tetrachloride and 100 ml of methylene chloride was treated with 45 g (0.252 mole) of p-chlorobenzenesulfenyl chloride. The reaction mixture was allowed to stand seven days at 23° C. Filtration through a thin layer of clay removed a small amount of flocculent solid. Evaporation of the filtrate at reduced pressure gave 51.5 g (60%) of crude product, m.p. 60°. Recrystallization from a mixture of 100 ml of ethyl acetate and 30 ml of pentane gave pure product m.p. 79°–81°.

Anal. Calc'd. for $C_{14}H_{12}Cl_2O_2S_2$: C,48.42; H,3.48; Cl,20.42; S,18.47. Found: C,48.57; H,3.44; Cl,20.34; S,18.13.

EXAMPLE 21

PREPARATION OF 1-(PHENYLSULFONYL)VINYL m-TOLYL SULFIDE

To a solution of 12.7 g (39 mmoles) of 2-chloro-1-(phenylsulfonyl)ethyl m-tolyl sulfide in 50 ml of tetrahydrofuran at 25° was added 5.4 ml (3.94 g, 39 mmoles) of triethylamine. Colorless crystals began to separate at once and an exotherm to 40° C. occurred. Filtration after 20 minutes separated 4.10 g (77%) of triethylamine hydrochloride, m.p. 255°–257°. Evaporation of the filtrate left a residue of 12.4 g of crude solid product which was recrystallized from 30 ml of ethanol and 8 ml of water to give 9.5 g (84%) of pure 1-phenyl-sulfonylvinyl m-tolyl sulfide, m.p. 79.5°–80.5°.

EXAMPLE 22

PREPARATION OF p-BROMOPHENYL 1-(p-CHLOROPHENYLSULFONYL)VINYL SULFIDE

Thirty-five grams (82 mmoles) of 2-chloro-1-(p-chlorophenylsulfonyl)ethyl p-bromophenyl sulfide was dissolved in 100 ml of tetrahydrofuran and treated with 12 ml (86 mmoles) of triethylamine. The mixture was diluted with 100 ml of diethyl ether and allowed to stand for 15 minutes. The precipitated triethylamine hydrochloride was separated by filtration. Evaporation of solvent from the filtrate gave 35 g of crude solid m.p. 45°–95°. Recrystallization from 100 ml of ethyl acetate-pentane (45:55) gave 13 g of pure product, m.p. 97°–99°.

Anal. Calc'd. for $C_{14}H_{10}BrClO_2S_2$: C,43.15; H,2.59; Br,20.50; Cl,9.10; S,16.45. Found: C,43.17; H,2.55; Br,20.60; Cl,9.14; S,16.64.

EXAMPLE 23

PREPARATION OF p-t-BUTYLPHENYL-1-(PHENYLSULFONYL)VINYL SULFIDE

To a solution of 15.0 g (40.7 mmoles) of 2-chloro-1-(phenylsulfonyl)ethyl p-t-butylphenyl sulfide in 85 ml of tetrahydrofuran was added first 100 ml of diethyl ether and then 5.66 ml (4.13 g, 40.8 moles) of triethylamine. The reaction mixture was allowed to stand for 90 minutes. Filtration removed 5.2 g (93%) of triethylamine hydrochloride, m.p. 255°–256°. Evaporation of the mixed ether solvent left a residue of 13 g (97%) of crude product, m.p. 55°–57°. Recrystallization from 17 ml of ethyl acetate and 28 ml of pentane gave 11.2 g (83%) of pure material, m.p. 57°–58°.

Anal. Calc'd. for $C_{18}H_{20}O_2S_2$: C,65.02; H,6.06; S,19.29. Found: C,65.55; H,6.21; S,19.23.

EXAMPLE 24

PREPARATION OF p-BROMOPHENYL 1-(m-NITROPHENYLSULFONYL)VINYL SULFIDE

2-Chloro-1-(m-nitrophenylsulfonyl)ethyl p-bromophenyl sulfide (27.1 g, 62.1 mmoles) was dissolved in 125 ml of tetrahydrofuran. The solution was diluted with 125 ml of diethyl ether and treated with 8.65 ml (6.3 g, 62.3 mmoles) of triethylamine. After one hour the mixture was filtered to remove 7.52 g (88%) of triethylamine hydrochloride, m.p. 255°–258°. Removal of solvent from the filtrate gave a yellow oil which crystallized upon scraping. Recrystallization from 25 ml of ethyl acetate and 10 ml of pentane gave 12 g (48%) of product m.p. 109°–111°.

Anal. Calc'd. for $C_{14}H_{10}BrNO_4S_2$: C,42.01; H,2.52; Br,19.96; N,3.50; S,16.02. Found: C,42.06; H,2.54; Br,19.59; N,3.50; S.15.78.

EXAMPLE 25

PREPARATION OF 1-(p-CHLOROPHENYLSULFONYL)VINYL PHENYL SULFIDE

To a solution of 30 g (86.5 mmoles) of 2-chloro-1-(p-chlorophenylsulfonyl)ethyl phenyl sulfide in 100 ml of tetrahydrofuran was added 12.2 ml (8.88 g, 87.8 mmoles) of triethylamine. After two hours the reaction mixture was filtered to remove triethylamine hydrochloride. The filtrate was evaporated down under reduced pressure, first at 15 mm and finally at 0.01 mm (25° C.), to give a light yellow oil.

Anal. Calc'd. for $C_{14}H_{11}ClO_2S_2$: C,54.10; H,3.56; Cl,11.41; S,20.63. Found: C,53.50; H,3.72; Cl,11.50; S,19.83.

EXAMPLE 26

PREPARATION OF p-BROMOPHENYL 1-(PHENYLSULFONYL)VINYL SULFIDE

A solution of 10.2 g (26.1 mmoles) of 2-chloro-1-(phenylsulfonyl)ethyl p-bromophenyl sulfide in 50 ml of tetrahydrofuran was diluted with 50 ml of diethyl ether and treated with 3.63 ml (2.65 g, 26.2 mmoles) of triethylamine. After 20 minutes the triethylamine hydrochloride was removed by filtration. The filtrate was freed of solvent by evaporation under reduced pressure to leave a viscous, pale yellow oil of $n^{20}$ 1.6338.

Anal. Calc'd. for $C_{14}H_{11}BrO_2S_2$: C,47.33; H,3.12; Br,22.49. Found: C,46.54; H,3.11; Br,23.17.

EXAMPLE 27

PREPARATION OF p-t-BUTYLPHENYL 1-(p-CHLOROPHENYL SULFONYL)VINYL SULFIDE p-t-Butylphenyl 1-(p-chlorophenylsulfonyl)-2-chloroethyl sulfide (16.12 g, 40.0 mmoles) was dissolved in 80 ml of tetrahydrofuran at 25° C. The solution was treated with 5.6 ml (4.08 g, 40.3 mmoles) of triethylamine and allowed to stand for 30 minutes. After filtration had separated the triethylamine hydrochloride, the filtrate was freed of solvent by evaporation at reduced pressure. The residue was a colorless solid, m.p. 74°–79°. Recrystallization from 25 ml of ethanol gave 12.2 g (84%) of pure product m.p. 79°–81°.

Anal. Calc'd. for $C_{18}H_{19}ClO_2S_2$: C,58.92; H,5.22; Cl,9.66; S,17.47. Found: C,58.75; H,5.23; Cl,9.55; S,16.59.

EXAMPLE 28

PREPARATION OF 1-(p-t-BUTYLPHENYLSULFONYL VINYL PHENYL SULFIDE

To a solution of 12.9 g (35.0 mmoles) of 2-chloro-1-(p-t-butylphenylsulfonyl)ethyl phenyl sulfide in 50 ml of tetrahydrofuran at 23° C. was added 5.5 ml (4.0 g, 39.5 mmoles) of triethylamine. Filtration after three hours separated 4.5 g (94%) of triethylamine hydrochloride, m.p. 258°. Solvent was removed from the filtrate by evaporation at reduced pressure to give 12.1 g of pale yellow oil.

Anal. Calc'd. for $C_{18}H_{20}O_2S_2$: C,65.02; H,6.06; S,19.29. Found: C,65.03; H,6.15; S,19.36.

EXAMPLE 29

PREPARATION OF p-CHLOROPHENYL-1-(PHENYLSULFONYL)VINYL SULFIDE

A solution of 11.5 g (33.2 millimoles) of 2-chloro-1-phenylsulfonylethyl p-chlorophenyl sulfide in 50 ml of tetrahydrofuran was treated with 6.0 ml (4.37 g, 43.2 millimoles) of triethylamine at 23° C. Filtration after 2.5 hours separated 4.8 g (104%) of triethylamine hydrochloride, m.p. 251°. Evaporation of the filtrate gave 9.0 g (87%) of pale yellow oil which after vacuum drying for 16 hours at 23° (0.01 mm) had $n^{20}$ 1.6200.

Anal. Calc'd. for $C_{14}H_{11}ClO_2S_2$: C,54.10; H,3.57; Cl,11.41; S,20.63. Found: C,53.77; H,3.55; Cl,11.35; S,20.71.

The microbicides of this invention may be applied prior to infestation or after attack has begun. To evaluate the microbicides of the instant invention they were tested against Tomato Early Blight, *Alternaria sp; Pythium sp; Fusarium sp;* and Rhizoctonia. The microbicide was applied as an emulsion in water prepared from an acetone solution at varying concentrations. The results are shown in Table I.

TABLE I

SUMMARY OF BIOLOGICAL TESTING

A-ADDUCTS

| | | % Control of Tomato Early Blight at at Specified Concn. in ppm | | | | | | | % Control of Microbes at 500 ppm[a] | | | |
|---|---|---|---|---|---|---|---|---|---|---|---|---|
| Run | W | Y | 500 | 250 | 125 | 62 | 31 | 16 | 8 | A | P | F | R |
| 1 | p-CH$_3$ | m-CH$_3$ | 99 | 93 | 84 | 79 | 63 | 48 | | 100 | 95 | 45 | 100 |
| 2 | p-CH$_3$ | H | | | | | 96 | 88 | 73 | 100 | 45 | 50 | 82 |
| 3 | p-CH$_3$ | p-Br | 75[b] | | | | | | | 45 | | 90 | 85 |
| 4 | p-CH$_3$ | m-NO$_2$ | | | | | | | | | | | |
| 5 | H | p-t-Bu | 70 | 50 | 35 | | | | | 80 | 80 | 0 | 85 |
| 6 | H | m-CH$_3$ | 100 | 99 | 95 | 93 | 85 | | | 100 | 100 | 100 | 82 |
| 7 | H | H | 90[b] | | | | | | | | | | |
| 8 | H | p-Br | 98 | 88 | 79 | 51 | 27 | | | 100 | 20 | 100 | 5 |
| 9 | p-Cl | p-t-Bu | | | | | | | | 40 | 45 | 95 | 90 |
| 10 | p-Cl | H | 90[b] | | | | | | | 100 | 100 | 100 | 94 |
| 11 | p-Cl | p-Br | 50[b] | | | | | | | 100 | 25 | 80 | 20 |
| 12 | p-Cl | m-NO$_2$ | 97 | 92 | 82 | 61 | 56 | | | 50 | 95 | 95 | 60 |
| 13 | m-NO$_2$ | H | 99 | 98 | 94 | 95 | | | | 100 | 40 | 40 | 45 |
| 14 | m-NO$_2$ | p-Br | 97 | 93 | 89 | 73 | 56 | | | 100 | 80 | 40 | 55 |
| 15 | m-NO$_2$ | m-NO$_2$ | 100 | 99 | 76 | 64 | | | | 60 | 35 | 90 | 61 |

B-OLEFINS SULFIDES

| | | % Control of Tomato Early Blight at at Specified Concn. in ppm | | | | | | | % Control of Microbes at 500 ppm[a] | | | |
|---|---|---|---|---|---|---|---|---|---|---|---|---|
| Run | W | Y | 500 | 250 | 125 | 62 | 31 | 16 | 8 | A | P | F | R |
| 16 | p-CH$_3$ | H | 98 | 92 | 84 | 64 | 60 | | | 100 | 100 | 100 | 88 |
| 17 | H | p-t-Bu | 74 | 42 | 29 | | | | | 100 | 80 | 0 | 75 |
| 18 | H | m-CH$_3$ | | | | | | | | | | | |
| 19 | H | H | 99[b] | | | | 96 | 87 | 77 | | | | |
| 20 | H | p-Br | 99 | 97 | 76 | 69 | 41 | 26 | | 100 | 100 | 45 | 100 |
| 21 | p-Cl | p-t-Bu | | | | | | | | 35 | 45 | 90 | 100 |
| 22 | p-Cl | H | 100 | 99 | 63 | | | | | 50 | 95 | 0 | 100 |
| 23 | p-Cl | p-Br | 81[b] | | | | | | | 100 | 80 | 55 | 35 |
| 24 | m-NO$_2$ | p-Br | 100 | 99 | 75 | 60 | 50 | | | 75 | 95 | 0 | 57 |
| Standard | | | | | | | | | | | | | |
| TDQ/H184 | | | | | | | 96 | 89 | | 96 | | | |

[a] A = Alternaria sp., P = Pythium sp., F = Fusarium sp., R = Rhizoctonia sp.
[b] At 1000 ppm.

The microbicides of this invention were tested against various prior art compounds. These comparative results appear below in Table II.

TABLE II

COMPARATIVE TESTS WITH PRIOR ART COMPOUNDS

| Structure | Test | % Control Alternaria solani at 500 ppm | Source |
|---|---|---|---|
| (structure) | 1 | 45 | U.S. Pat. No. 4,031,247 |
| (structure) | 2 | 55 | U.S. Pat. No. 4,031,247 |
| (structure) | 3 | 80 | Uniroyal |
| (structure) | 4 | 85 | Instant Invention |
| (structure) | 5 | 15 | U.S. Pat. No. 4,031,247 |
| (structure) | 6 | 45 | U.S. Pat. No. 4,031,247 |
| (structure) | 7 | 60 | Uniroyal |

TABLE II-continued
COMPARATIVE TESTS WITH PRIOR ART COMPOUNDS

| | | | |
|---|---|---|---|
| 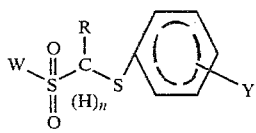 | 8 | 90 | Instant Invention |

What is claimed is:

1. A microbicide having the general formula

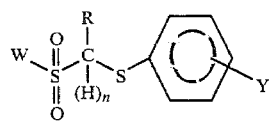

wherein n is 0 or 1; R is a halomethyl or methylene radical; W is cyclohexyl, or meta or para substituted phenyl wherein the substituents are selected from the group consisting of $C_1$–$C_4$ alkyl, halogen and nitro; Y is hydrogen, halogen, nitro or $C_1$–$C_4$ alkyl; provided that when R is halomethyl, n is 1, and when R is methylene, n is 0.

2. The compound according to claim 1 wherein R is a halomethyl radical.

3. The compound according to claim 2 wherein the halomethyl radical is chloromethyl.

4. The compound according to claim 2 wherein W is p-methylphenyl or p-chlorophenyl.

5. The compound according to claim 2 wherein Y is hydrogen or p-t-butyl.

6. The compound according to claim 2 wherein W is m-nitrophenyl and Y is p-bromo.

7. The compound according to claim 1 wherein R is a methylene radical.

8. The compound according to claim 7 wherein W is a phenyl and Y is p-t-butyl, m-methyl or p-bromo.

9. The compound according to claim 7 wherein W is p-methylphenyl and Y is m-methyl, p-bromo, m-nitro or hydrogen.

10. The compound according to claim 7 wherein Y is p-t butyl, m-methyl, p-bromo or hydrogen.

11. The compound according to claim 7 wherein W is m-nitrophenyl and Y is p-bromo, m-nitro or hydrogen.

12. The compound of claim 2 wherein W is cyclohexyl and Y is hydrogen.

13. A microbicide having the general formula

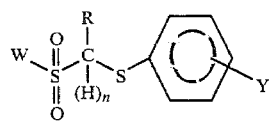

wherein n is 0 or 1; R is a halomethyl or methylene radical; W is cyclohexyl, phenyl or meta or para substituted phenyl wherein the substituents are selected from the group consisting of $C_1$–$C_4$ alkyl, halogen and nitro, Y is halogen, nitro or $C_1$–$C_4$ alkyl; provided that when R is halomethyl, n is 1, and when R is methylene, n is 0.

14. The compound according to claim 13 wherein R is halomethyl.

15. The compound according to claim 14 wherein the halo methyl radical is chloromethyl.

16. The compound according to claim 14 wherein W is p-methylphenyl, p-chlorophenyl, or m-nitrophenyl.

17. The compound according to claim 13 wherein R is a methylene radical, W is phenyl or p-methylphenyl and Y is m-methyl, p-bromo or m-nitro.

18. A method for controlling microbes which comprises applying to a plant to be protected against attack by such microbes, a microbicidally effective amount of a compound selected from the formula

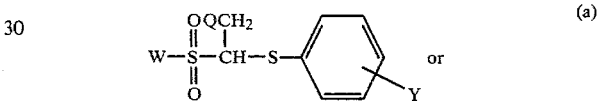 (a)

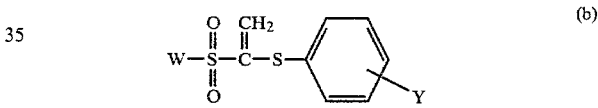 (b)

wherein Q is halogen, W is cyclohexyl, phenyl, or meta or para substituted phenyl wherein the substituents are $C_1$–$C_4$ alkyl, halogen or nitro, Y is hydrogen, halogen, nitro or $C_1$–$C_4$ alkyl.

19. The method according to claim 18 wherein W is p-methylphenyl and Y is m-methyl or hydrogen.

20. The method according to claim 18 wherein W is phenyl and Y is m-methyl or p-bromo.

21. The method according to claim 18 wherein W is p chlorophenyl and Y is p-bromo or hydrogen.

* * * * *